United States Patent
Zugates et al.

(10) Patent No.: US 11,207,074 B2
(45) Date of Patent: Dec. 28, 2021

(54) METHODS, DEVICES AND SYSTEMS FOR FILLING BODY CAVITIES

(71) Applicant: ARSENAL MEDICAL, INC., Watertown, MA (US)

(72) Inventors: Gregory T. Zugates, Chelmsford, MA (US); Joseph Lomakin, Cambridge, MA (US); Jennifer Mortensen, Athens, GA (US); Jeffrey Groom, II, Medford, MA (US); John Marini, Weymouth, MA (US); Stephanie Webber, Brookline, MA (US)

(73) Assignee: Arsenal Medical, Inc., Watertown, MA (US)

( * ) Notice: Subject to any disclaimer, the term of this patent is extended or adjusted under 35 U.S.C. 154(b) by 408 days.

(21) Appl. No.: 15/944,154

(22) Filed: Apr. 3, 2018

(65) Prior Publication Data
US 2018/0221031 A1  Aug. 9, 2018

Related U.S. Application Data

(63) Continuation of application No. 14/862,043, filed on Sep. 22, 2015, now Pat. No. 9,999,427.

(60) Provisional application No. 62/053,546, filed on Sep. 22, 2014.

(51) Int. Cl.
| | |
|---|---|
| *A61B 17/12* | (2006.01) |
| *A61B 17/00* | (2006.01) |
| *A61M 25/00* | (2006.01) |
| *A61M 5/315* | (2006.01) |

(52) U.S. Cl.
CPC .... *A61B 17/12186* (2013.01); *A61B 17/0057* (2013.01); *A61B 17/12181* (2013.01); *A61B 17/12195* (2013.01); *A61M 5/31596* (2013.01); *A61M 25/0026* (2013.01); *A61B 2017/00495* (2013.01); *A61B 2017/00646* (2013.01); *A61B 2017/1205* (2013.01)

(58) Field of Classification Search
CPC .......... A61B 17/0057; A61B 17/12181; A61B 17/12195; A61M 25/0026
See application file for complete search history.

(56) References Cited

U.S. PATENT DOCUMENTS

| | | | | |
|---|---|---|---|---|
| 8,641,666 B2 * | 2/2014 | El-Nounou | ....... | A61M 25/0082 604/107 |
| 9,050,414 B2 * | 6/2015 | Schoenle | ............ | B01F 13/0818 |
| 2003/0216685 A1 * | 11/2003 | Porter | .............. | A61B 17/12136 604/82 |
| 2009/0209916 A1 * | 8/2009 | Peindl | .............. | A61B 17/00491 604/173 |
| 2012/0041359 A1 * | 2/2012 | Schoenle | ............ | B01F 11/0054 604/22 |

(Continued)

FOREIGN PATENT DOCUMENTS

WO     2018081837 A2    5/2018

*Primary Examiner* — Julie A Szpira
(74) *Attorney, Agent, or Firm* — Kacvinsky Daisak Bluni PLLC

(57) ABSTRACT

In various aspects, present disclosure is directed to methods, devices and systems whereby one or more low viscosity fluids may be introduced into a catheter and whereby the one or more low viscosity fluids may be converted into a high viscosity fluid in the catheter, which high viscosity fluid may be delivered from an exit port of the catheter.

17 Claims, 4 Drawing Sheets

(56) References Cited

U.S. PATENT DOCUMENTS

| | | | | |
|---|---|---|---|---|
| 2012/0265287 A1* | 10/2012 | Sharma | ............... | A61L 31/18 623/1.11 |
| 2013/0317418 A1* | 11/2013 | Freyman | ............... | A61M 37/00 604/24 |
| 2016/0256170 A1* | 9/2016 | Busold | ............... | A61M 25/0067 |

* cited by examiner

METHODS, DEVICES AND SYSTEMS FOR FILLING BODY CAVITIES

CROSS-REFERENCE TO RELATED APPLICATIONS

This application is a continuation of U.S. application Ser. No. 14/862,043, filed Sep. 22, 2015, which claims priority under 35 U.S.C. § 119 to U.S. Provisional Patent Application No. 62/053,546 by Gregory Zugates et al. filed Sep. 22, 2014 and titled "Methods, Devices and Systems for Filling Body Cavities." The entire disclosure of this reference is incorporated herein in its entirety and for all purposes.

FIELD

Methods, devices and systems for filling body cavities are generally described.

BACKGROUND

Controlling fluid, gas or material movement in the body has numerous clinical applications and benefits, including controlling hemorrhage, preventing aneurysm growth or risk of rupture, treating tumors and managing respiratory disorders. These treatments often require introduction of a material to fill or partially fill a space, potential space, vessel, cavity or other volume inside and/or on the surface of the body. However, movement of that material outside the targeted treatment zone may have undesirable effects, cause complications, limit efficacy or lead to morbidity or mortality, among other consequences.

One clinical application in which polymers or other materials have been used to control movement of bodily fluids is in the treatment of aneurysms. Generally, an aneurysm is an abnormal widening or ballooning of a portion of a blood vessel due to weakness in the vessel wall. If left untreated, aneurysms can grow large and rupture, causing internal bleeding which is often fatal. Two locations in which aneurysms are commonly found are in the abdominal aorta and the brain. Other clinical applications in which polymers or other materials have been used to control movement of bodily fluids include filling arteriovenous malformations and blockage of feeder arteries for tumors (e.g., in the treatment of malignant and benign tumors such as kidney lesions, liver lesions, typically hepatocellular carcinoma, and uterine fibroids).

The present disclosure is directed to methods, devices and systems for performing these and other clinical procedures.

SUMMARY

In various aspects, present disclosure is directed to methods, devices and systems whereby one or more low viscosity fluids may be introduced into a catheter and whereby the one or more low viscosity fluids may be converted into a high viscosity fluid, which high viscosity fluid may be delivered from an exit port of the catheter.

In some aspects, the present disclosure is directed to a system comprising (a) a catheter comprising a first lumen having a proximal end and a distal end and an exit port proximal to a distal end of the catheter and (b) a first low viscosity fluid. The catheter may be configured to receive the first low viscosity fluid at the proximal end of the first lumen, form a high viscosity fluid from the first low viscosity fluid, and deliver the high viscosity fluid from the exit port of the catheter.

In various embodiments, the system may be configured to form the high viscosity liquid within 5 cm of the exit port of the catheter.

In various embodiments, the high viscosity liquid may be formulated to further cure into a solid material after delivery from the exit port of the catheter.

In some embodiments, the first low viscosity fluid undergoes an increase in viscosity upon exposure to light or heat, and the catheter further comprises a source of heat or light and is configured to expose the first low viscosity fluid to light or heat such that the first low viscosity fluid is converted to the high viscosity fluid. For example, the first low viscosity fluid may comprise a polyisocyanate and an amine catalyst and may be converted to the high viscosity fluid upon exposure to heat. As another example, the first low viscosity fluid may comprise an acrylate and a diacrylate and may be converted to the high viscosity fluid upon exposure to UV light.

In some aspects, the present disclosure is directed to a system comprising (a) a catheter comprising a first lumen having a proximal end and a distal end, a second lumen having a proximal end and a distal end, and an exit port proximal to a distal end of the catheter, (b) a first low viscosity fluid and (c) a second low viscosity liquid. The catheter may be configured to receive the first low viscosity fluid at the proximal end of the first lumen and to receive the second low viscosity fluid at the proximal end of the second lumen. The catheter may also be configured to mix the first low viscosity fluid and the second low viscosity fluid to form a high viscosity fluid and to deliver the high viscosity fluid from the exit port of the catheter.

In various embodiments, the system may be configured to form the high viscosity liquid within 5 cm of the exit port of the catheter.

In various embodiments, high viscosity liquid is formulated to further cure into a solid material after delivery from the exit port of the catheter (e.g., by providing a curing agent in one of the first and second low viscosity fluids that causes crosslinking within the high viscosity fluid after delivery from the exit port).

In some embodiments, the first low viscosity fluid may comprise a multi-functional isocyanate and the second low viscosity fluid may comprise a multi-functional nucleophilic species.

In embodiments where a curing agent is provided, (a) the curing agent may be one that reacts with water to form a multi-functional nucleophilic curing species (e.g., the multi-functional nucleophilic curing species may be a multi-functional amine, such as that provided by a multi-functional imine curing agent such as a multifunctional ketimine), (b) the curing agent may be a multi-functional nucleophilic curing species that reacts more slowly with the diisocyanate than the difunctional nucleophilic species, or (c) the curing agent may be a multi-functional curing species that reacts more slowly with the difunctional nucleophilic species than the diisocyanate, among other possibilities.

In embodiments where a curing agent is provided and where the difunctional nucleophilic species is a difunctional amine, (a) the diisocyanate may be over indexed and the curing agent may be adapted to react with water in the body to cause crosslinking, (b) the diisocyanate may be over indexed and the curing agent may be an isocyanate-reactive species that reacts more slowly with the diisocyanate compared to the difunctional amine, or (c) the difunctional amine may be over indexed and the curing agent may be selected from an epoxide, alkyl chloride, an acrylate and an acrylamine, among other possibilities.

In some embodiments, the first low viscosity fluid may comprise a diisocyanate and the second low viscosity fluid may comprise a difunctional nucleophilic species selected from a difunctional amine (also referred to herein as a diamine) and a difunctional thiol (also referred to herein as a dithiol), among other possibilities.

In some embodiments, the first low viscosity fluid may comprise a polyisocyanate and the second low viscosity fluid may comprise water and, optionally, a multi-functional alcohol.

In some embodiments, the first low viscosity fluid may comprise diglycidyl ether and the second low viscosity fluid may comprise a diamine or dithiol and, optionally, a multi-functional alcohol In some embodiments, the first low viscosity fluid may comprise divinyl sulfone and the second low viscosity fluid may comprise a diamine or a dithiol and, optionally, a multi-functional alcohol.

In some embodiments, the first low viscosity fluid may comprise a hydride siloxane and the second low viscosity fluid may comprise a vinyl siloxane and, optionally, a multi-functional alkene.

In some aspects, the present disclosure is directed to a method of treating a body cavity comprising introducing a first low viscosity fluid into a proximal end of a first lumen of a catheter and delivering a high viscosity liquid from an exit port of the catheter into the body cavity.

In some embodiments, the method comprises exposing the low viscosity fluid to light or heat within the catheter such that the low viscosity fluid is converted to the high viscosity fluid that is delivered from the exit port of the catheter into the body cavity. The body cavity may be, for example, a vascular lumen selected from an artery supplying a tumor, an aneurysm and an arteriovenous malformation, among numerous other possibilities.

In some embodiments, the method further comprises introducing a second low viscosity fluid into a proximal end of a second lumen of the catheter, in which case the first low viscosity fluid and the second low viscosity fluid may be mixed to form the high viscosity fluid that is delivered from the exit port of the catheter into the body cavity.

In some aspects, the present disclosure is directed to a catheter comprising (a) a first lumen having a proximal end and a distal end and (b) an exit port proximal a distal end of the catheter, the catheter being configured receive a first low viscosity fluid at the proximal end of the first lumen, form a high viscosity liquid within 5 cm of the exit port, and deliver a high viscosity fluid from the exit port of the catheter.

In some embodiments, the catheter further comprises a source of heat or light and is configured to expose the first low viscosity fluid to light or heat such that the first low viscosity fluid is converted to the high viscosity fluid within 5 cm of the exit port. For example the catheter may comprise a source of ultraviolet light or the catheter may comprise a source of thermal energy or radiofrequency energy, among other possibilities.

In some embodiments, the catheter may further comprise a second lumen having a proximal end and a distal end, the catheter may be configured receive a second low viscosity fluid at the proximal end of the second lumen, and the catheter may be configured to mix the first low viscosity fluid and the second low viscosity fluid within 5 cm of the exit port thereby forming the high viscosity fluid. The catheter may, for example, comprise a passive mixer (e.g., a T-mixer, static helical mixer, lamination mixer, etc.) and/or a dynamic mixer (e.g., rotating mixing element, ultrasonic mixer, etc.).

In some embodiments, the catheter may comprise an elastic tip that increases in diameter as a result of pressure exerted by the high viscosity fluid.

In some embodiments, the catheter may comprise a self-expanding tip.

Advantages of various aspects and embodiments of the present disclosure include one or more of the following, among others: (a) the ability to use low profile catheters for the delivery of high viscosity materials to a target body cavity, (b) the ability to repeatedly stop and start the flow through such catheters, (c) the ability to deliver high viscosity materials that are retained within a target body cavity, and (d) the ability to deliver materials that conform to, or take the shape of, and may be compliant with, a target body cavity.

These and other aspects, embodiments and advantages of the present disclosure will become apparent to those of ordinary skill in the art upon review of the detailed description set forth below.

DETAILED DESCRIPTION

Figure 1A:
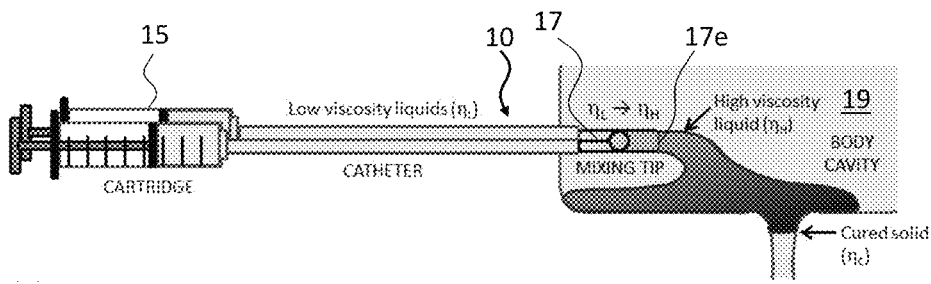
FIG. 1A is a schematic illustration of a system wherein one or more low viscosity liquid formulations undergo an increase in viscosity and then injected into a body cavity using a catheter with an activation tip (a mixing tip in the embodiment shown), in accordance with an embodiment of the present disclosure.

A more complete understanding of the present invention is available by reference to the following detailed description of numerous aspects and embodiments of the invention. The detailed description which follows is intended to illustrate but not limit the invention.

This present disclosure pertains to systems, methods and devices for delivery of a high viscosity fluid into a body cavity. In certain embodiments, the high viscosity fluid is subsequently further cured into a solid material after delivery within the body cavity. As used herein, a "solid" material is a material that, when placed in a container, maintains its shape and does not flow, rather than assuming the shape of the container or flowing.

In various embodiments, one or more low viscosity fluids are mixed within a catheter to form a high viscosity fluid. In various embodiments, the catheter is a low profile catheter having a diameter of 7F (2.33 mm) or less, 6F (2 mm) or less, 5F (1.67 mm) or less, 4F (1.33 mm) or less, or even 3F (1 mm) or less in some embodiments.

Broadly, the high viscosity fluid will have a viscosity that is higher than the viscosity of each of the one or more low viscosity fluids, typically at least 10 times greater than the viscosity of each or the one or more low viscosity fluids, more typically at least 1,000 times greater than the viscosity of each or the one or more low viscosity fluids. (Conversely, each of the one or more low viscosity fluids broadly will have a viscosity that is lower than the viscosity of the high viscosity fluid, typically at least 10 times less than the viscosity of the high viscosity fluid, more typically at least 1,000 times less than the viscosity of the high viscosity fluid.) In certain beneficial embodiments, the high viscosity fluid has a viscosity between 100,000 centipoise (cP) and 1,000,000 cP or more as measured using a parallel plate rheometer with a shear rate between 1 and 10 $s^{-1}$. In certain beneficial embodiments, the one or more low viscosity fluids each may have a viscosity of 200 centipoise (cP) or less as measured using a parallel plate rheometer.

In various embodiments, the one or more low viscosity fluids will travel as such through most of the catheter length but will rapidly increase in viscosity near the point of exit from the catheter (e.g., within the last 5 cm of travel through the catheter prior to exiting the catheter, within the last 2.5 cm of travel through the catheter, within the last 1 cm of travel through the catheter, or even within the last 0.5 cm or less of travel through the catheter) such that a high viscosity fluid exits the catheter and is deposited in a body cavity. In certain beneficial embodiments, the high viscosity fluid undergoes curing after being deposited in the body cavity via a suitable mechanism.

Such systems are particularly advantageous for filling body cavities or vessels that are open or contain high bodily fluid flow rates, where it is important to localize the formulation proximal to the injection site (e.g., to prevent distal embolization of non-target tissue). Procedures that may be performed in conjunction with the systems described herein include the filling of aneurysms that contain blood flow from inlet/outlet blood vessels (e.g., abdominal aortic aneurysms), vascular embolization procedures (particularly those where local control is important), and filling of arteriovenous malformations, among many other possible procedures.

Figure 1B:
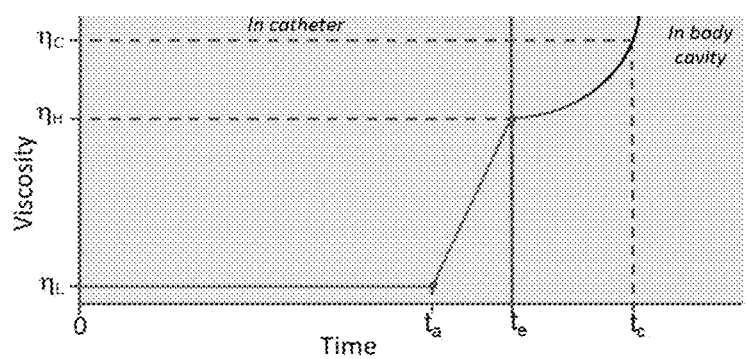
FIG. 1B is a schematic illustration of hypothetical viscosity vs. time profile for a unit volume of formulation, wherein the formulation viscosity is increased rapidly over a very short distance in the activation tip, and then continues to cure in the body cavity, in accordance with an embodiment of the present disclosure. The time course plotted is for a unit volume of formulation that is loaded and dispensed (where $t_a$=time to reach activation tip; $t_e$=time to reach catheter exit; $t_c$=time to reach curing; $\eta_L$=low viscosity; $\eta_H$=high (exit or dispensed) viscosity $\eta_C$=cured viscosity).

In an embodiment illustrated schematically in FIGS. 1A and 1B, at least one low viscosity fluid (a pair of low viscosity liquids is shown) having a viscosity $\eta_L$ is contained in a syringe, cartridge or other storage and dispensing device 15. The low viscosity fluid(s) is(are) then pushed into a catheter 10 having an activation tip (a mixing tip 17 in the embodiment shown) at time t=0, beneficially, a low profile catheter that is positioned for dispensing at the target site in a subject (i.e., a body cavity 19 to be at least partially filled). After a time $t_a$ the fluid(s) have traveled to a point that is near the exit port 17c of the catheter (e.g., within the 5 cm or less of the exit port 17e), at which point an activation mechanism leads to an increase in viscosity of the fluid(s) from a low viscosity $\eta_L$ to a high viscosity rm. Although the increase in fluid viscosity is caused by mixing of two low viscosity liquids in the embodiment shown, in other embodiments a single low viscosity fluid is subjected to activation conditions (e.g., a change in temperature, exposure to light, etc.). At a time $t_e$, the resulting high viscosity fluid exits the catheter and is dispensed into the body cavity, where it can further cure and increase in viscosity to an even higher viscosity $\eta_C$ (at time $t_C$) or cure into a solid material. An advantage of this design is the ability to deploy a high viscosity fluid using a low profile catheter, which is facilitated by generating the high viscosity fluid near the point of exit from the catheter, which minimizes the pressure drop within the catheter and thus the pressure required to deploy the formulation.

Various aspects of the system, as well as their design attributes and advantages, are summarized here:

Low Viscosity Liquid(s).

The use of low viscosity liquids permits the delivery of material with low pressures or deployment forces. This design permits the use of hand-actuated systems, either with or without simple mechanical leverage (e.g., springs, gears). In addition, because pressure drop is proportional to fluid viscosity and inversely proportional the fourth power of the catheter diameter (assuming the fluid is a non-compressible, Newtonian fluid in laminar flow in a tube), lower viscosity fluids permit the use of lower profile (diameter) catheters for a given pressure drop. This design feature is particularly important for minimally invasive devices that benefit from small catheter sizes (e.g., ≤7F).

Transition from Low to High Viscosity.

High formulation viscosities permit better control of delivery to a particular site and retention within the target body cavity compared to low viscosity formulations. However, for reasons stated above, a high viscosity liquid would require a large catheter diameter for delivery, which is limiting in many vascular, catheter-based procedures. This problem is addressed in the present disclosure, in which a low viscosity material is delivered over most of the catheter length, at which point the fluid increases to a desirable, high viscosity liquid (i.e., only near the tip). This rapid, localized viscosity transition can be accomplished by reacting lower molecular weight species in the low viscosity liquid to form higher molecular weight species, which are capable of further chemical reaction in the body cavity in some embodiments. For example, a rapid, localized viscosity transition may be accomplished by polymerization of lower molecular weight prepolymer in the low viscosity liquid to form a higher molecular weight prepolymer, which preferably is capable of further polymerization or curing in the body cavity. Examples of mechanisms to increase the viscosity of a prepolymer-containing liquid include mixing two reactive liquid phases, heating a thermally unstable liquid prepolymer formulation, or applying ultraviolet (UV) light to photopolymerize a liquid formulation, among others. Formulation Curing.

The high viscosity state of the formulation will enable it be retained within a body cavity and conform to an irregular shape (e.g., conforming to the shape of the body cavity). Depending on the application, the formulation may continue to flow over time and spread outside of the target region/cavity. In these cases, it is advantageous for the material to cure or crosslink into a solid, non-flowable mass so that it remains isolated within the target site. Furthermore, this transition will enable the material to provide mechanical support to the cavity and surrounding tissues.

As previously indicated, one mechanism for activating a first low viscosity fluid is to mix the first low viscosity fluid with a second low viscosity fluid which reacts very quickly (near instantaneously) with the first low viscosity fluid to create a high viscosity liquid. For example, a first low molecular weight, low viscosity fluid may be mixed and reacted with a second low viscosity fluid to create a high molecular weight, high viscosity liquid.

In various embodiments, the first low viscosity fluid comprises a multi-functional (i.e., having a functionality of 2 or more) isocyanate, typically, a diisocyanate, and the second low viscosity fluid comprises a multi-functional nucleophilic species, typically a difunctional nucleophilic species. Examples of nucleophilic species which react with isocyanates include amines (forming ureas or polyureas) and thiols (forming thiocarbamates or polythiocarbamates), alcohols (forming urethanes or polyurethanes) and water (forming ureas or polyureas as well as carbon dioxide).

More particularly, upon being mixed in an activation tip of a catheter (discussed in more detail below), a diisocyanate (e.g., a low molecular weight isocyanate-terminated polymer) reacts with a diamine (e.g., a low molecular weight amine-terminated polymer) to form a linear isocyanate-terminated polyurea with high molecular weight and high viscosity. In is embodiment, the diisocyanate is over-indexed (i.e., in excess) relative to the diamine, such that a linear isocyanate-terminated polyurea is formed (and isocyanate remains available for further reaction). In other embodiments, the diamine may be over-indexed relative to the diisocyanate such that a linear amine-terminated polyurea is formed (and amine remains available for further reaction).

In one particular embodiment, a linear silicone polyurea, for example, a polydimethylsiloxane (PDMS) based urea, is formed by admixing two low-viscosity di-functional silicones, for example, by mixing a low viscosity isocyanate-terminated silicone with a low viscosity amine-terminated silicone. One example of a low viscosity isocyanate-terminated silicone is PDMS diisocyanate, for example as shown in formula [II]:

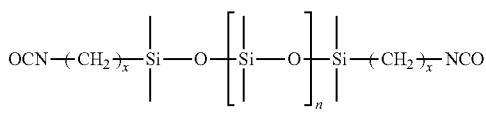

[II]

In the formula, x is an integer beneficially ranging, for example, from 1 to 10, among other possible values, more preferably from 1 to 5, even more preferably 3, and n is an integer ranging, for example, from 5 to 300, among other possible values, more preferably from 5 to 80. One example of a low viscosity amine-terminated silicone is PDMS diamine, for example as shown in Formula below,

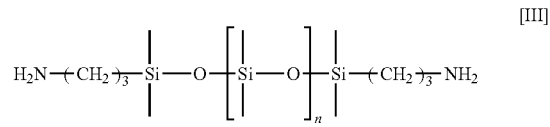

[III]

where n is an integer independently ranging, for example, from 5 to 300, among other possible values, more preferably from 5 to 80.

Figure 3:
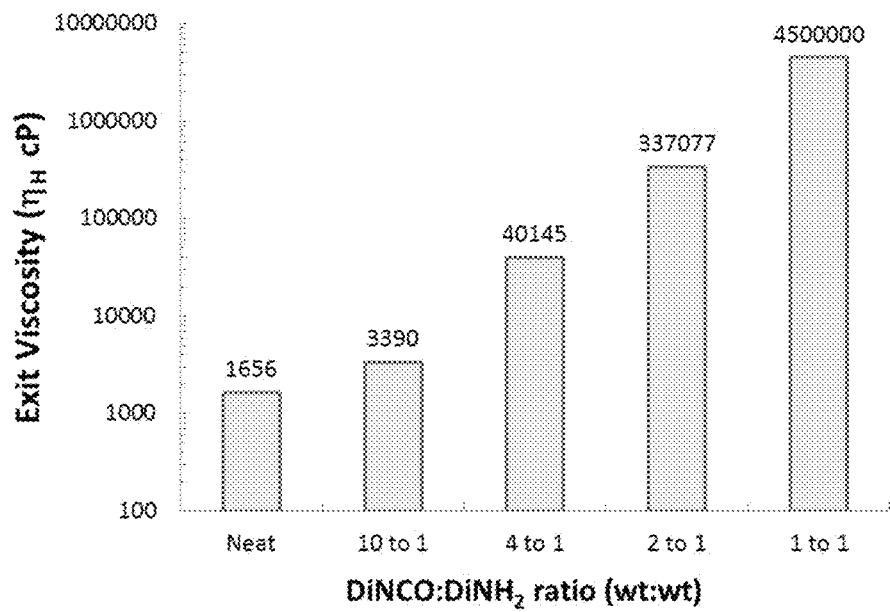
FIG. 3 is a bar graph illustrating exit viscosity as a function of diisocyanate-to-diamine ratio ($DiNCO:DiNH_2$), in accordance with an embodiment of the present disclosure.

Importantly, the high exiting viscosity ($\eta_H$) can be controlled over several orders of magnitude by adjusting the ratio between the diisocyanate and the diamine (DiNCO:DiNH$_2$). In this regard, FIG. 3 graphically illustrates exit viscosity as a function of the DiNCO:DiNH$_2$ ratio. The neat condition is pure diisocyanate, prepared by reacting Gelest carbinol DMS-C21 (a hydroxypropyl-terminated polydimethylsiloxane, 500-1000 mol. wt., available from Gelest, Inc., Morrisville, Pa., USA) with excess isophorone diisocyanate (IPDI). The diamine used is Gelest DMS-A21, an aminopropyl-terminated PDMS, mol. wt. 5000-7000, available from Gelest, Inc. As seen from FIG. 3, viscosity increases ~1300 times when the DiNCO:DiNH$_2$ ratio is varied from 10:1 to 1:1.

Furthermore, where over-indexing of either the diisocyanate or diamine is employed, the high molecular weight prepolymer formed is capable of further reaction at the chain termini. For example, over-indexing the isocyanate leads to a prepolymer than can further react with water in the body cavity (leading to further increases in molecular weight and viscosity), or with an added agent that leads to crosslinking.

Diisocyanate polymers can be prepared by several methods, including for example, phosgenation of polyamines (e.g., PDMS diamine), and Curtius rearrangement of acyl azides (prepared from diacids and/or diacid chlorides using trimethylsilyl azide). Diisocyanate polymers can be prepared by reaction of a difunctionalized polymer such as a diol polymer, diamine polymer, or diacid polymer, among others, with diisocyanate, in which case quasi-prepolymers may be formed (e.g., where excess or residual free isocyanate monomer is present) or strict-prepolymers may be formed (e.g., when just enough polyisocyanate is added to react with all functional sites available).

In some applications, the high viscosity fluid that exits the catheter may be the desired end product. However, in many cases, it is preferred to transition the material to a solid to provide mechanical support and long-term localization of the material (i.e., prevent flow or migration of the material out of the target area). A particularly beneficial mechanism for inducing fluid-to-solid transition is to add a curing agent (i.e., a crosslinking agent) to the formulation that acts independently, or substantially independently, of the reaction between the first and second low viscosity fluids. In this manner, the processes leading to viscosity increases and the processes leading to curing (i.e., crosslinking) can be independently controlled and designed.

In some embodiments, a curing agent is selected which reacts with water in the body to cause crosslinking. For example, in embodiments where a low viscosity fluid comprising a difunctional nucleophilic species is mixed with a low viscosity fluid comprising a diisocyanate, and where excess diisocyanate is employed, the curing agent may be a species which is substantially non-reactive with isocyanate before exposure to water, but which becomes reactive upon being exposed to water. In one specific example where a low viscosity fluid comprising a diamine is mixed with a low viscosity fluid comprising a diisocyanate, a multi-functional (i.e., having a functionality 2 or more) ketimine may be selected as a curing agent, for which exposure to water or moisture results in hydrolysis of the imine functionalities to form amines. The amines can then react with and cure the isocyanate-terminated high viscosity polyurea that is formed by prior reaction of the diamine and diisocyanate. In a particular embodiment, the ketimine is a low viscosity polymer, which can be made, for example, by a dehydration reaction between a multi-functional PDMS amine and methyl ethyl ketone (MEK) to yield a PDMS ketamine as shown in Formula [IV] below:

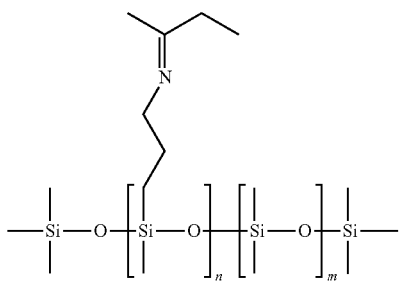

[IV]

In formula [IV], m is an integer ranging, for example, from 5 to 80, among other possible values, and n is an integer ranging, for example, from 2 to 10, among other possible values.

In some embodiments, a curing agent is selected which reacts more slowly than the primary reacting species. For example, in embodiments where a low viscosity fluid comprising a diamine is mixed with a low viscosity fluid comprising a diisocyanate, and where excess diisocyanate is employed, the curing agent may be a species that reacts more slowly with the isocyanate than amine. One specific example of such a species is a multi-functional alcohol (alcohols react approximately 1,000-fold slower than primary amines). A specific example of a multi-functional alcohol polymer is a low viscosity PDMS carbinol as shown in Formula [V] below:

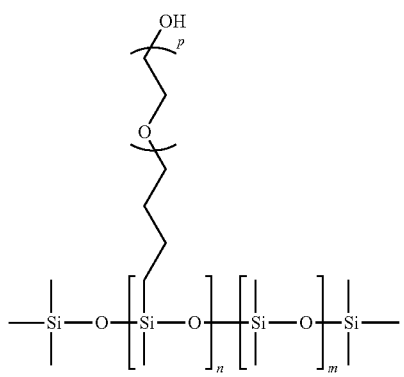

[V]

where m is an integer ranging, for example, from 5 to 80, among other possible values, n is an integer ranging, for example, from 2 to 10, among other possible values, and p is an integer ranging, for example, from 0 to 30 among other possible values.

As another example, in embodiments where a low viscosity fluid comprising a diamine is mixed with a low viscosity fluid comprising a diisocyanate, and where excess diamine is employed, the curing agent be a species that that reacts more slowly with the diamine than diisocyanate. Examples of such species include epoxides (e.g., trimethylolpropane triglycidyl ether, etc.), alkyl chlorides (e.g., dichlorohexane, etc.), acrylates (e.g., trimethylolpropane ethoxylate triacrylate, etc.), and acrylamides (e.g., N,N'-methylenebis(acrylamide), etc.).

Where a curing agent is selected which reacts more slowly than the primary reacting species, the slower cross-linking reaction enables the high viscosity prepolymer to mold or conform to the body cavity prior to solidification. By adjusting the amount of catalyst and the type/amount of curing agent, the curing rate may be independently tuned to occur over a clinically relevant time period, while allowing sufficient time for multiple stop/starts during the injection procedure (so that the catheter does not become plugged with cured material).

Additional examples of reactions which may be employed to produce high viscosity fluids from low viscosity fluids will now be described.

For example, in some embodiments, a low viscosity fluid comprising a multi-functional isocyanate polymer (i.e., having a functionality of 2, 3 or more) may be reacted with a low viscosity fluid comprising water (or bodily fluid) to form a fluid of increased viscosity that comprises a polyurea. Where the isocyanate is over-indexed relative to the water, a multi-functional alcohol may be employed as a curing agent.

As another example, in some embodiments, a low viscosity fluid comprising divinyl sulfone may be reacted with a low viscosity fluid comprising a diamine (e.g., PDMS diamine) to form a fluid of increased viscosity. Where the divinyl sulfone is over-indexed relative to the diamine, a multi-functional alcohol like that described above, among others, may be employed as a curing agent.

Thiols may be substituted for amines in various embodiments described herein.

As yet another example, in some embodiments, a low viscosity fluid comprising a hydride siloxane, for example, a polysiloxane containing reactive hydrogen-to-silicon bonds such as a hydrogen-terminated dimethyl polysiloxane may be reacted with a low viscosity fluid comprising a vinyl siloxane, for example, a vinyl terminated polysiloxane to form a fluid of increased viscosity. Where the hydride siloxane is over-indexed relative to the vinyl siloxane, a multi-functional alkene (e.g., triallyl isocyanurate, among others) may be employed as a curing agent.

As previously noted, in various embodiments of the disclosure, fluid viscosity is increased by subjecting a single low viscosity fluid to suitable activation conditions such as, for example, a change in temperature or exposure to light, among other possibilities.

In some embodiments, a low viscosity fluid is delivered along the length of a catheter and converted to a high viscosity liquid at the catheter tip by the application of heat. Further reaction or crosslinking preferably occurs in the body cavity to solidify the material and prevent continued flow.

One example of a heat activated formulation is one that comprises a multi-functional isocyanate mixed with an amine catalyst. In one embodiment, the multi-functional isocyanate is a silicone triisocyanate, specifically, an IPDI-terminated PDMS, prepared by reacting Gelest carbinol CMS-222 (a (hydroxypropyleneoxypropyl)methylsiloxane-dimethylsiloxane copolymer, also known as hydroxypropylene oxide modified polydimethylsiloxane, 5000-7000 mol. wt., available from Gelest, Inc.) with excess IPDI, and the amine catalyst is 1,8-diazabicycloundec-7-ene (DBU). This specific formulation will cure within several minutes at room temperature to form a crosslinked polyisocyanurate gel. Depending on the heat applied (i.e., the temperature increase applied to the formulation), the cure time may be reduced to several seconds or less. Because the material contains isocyanate groups, only partial curing may need to occur within the catheter tip (to increase viscosity), because further reaction that leads to full curing can be allowed to occur within the body cavity.

Other suitable formulations include those employing other combinations of species that react/cure within several minutes at room temperature, for example, an epoxy-amine system, among other possibilities. As above, depending on the heat applied to the formulation, the cure time may be reduced to several seconds or less.

In other embodiments, a low viscosity fluid is delivered along the length of a catheter and converted to a high viscosity liquid by irradiating the low viscosity fluid with visible or ultraviolet (UV) light at the catheter tip. Further reaction or crosslinking may be caused to occur in the body cavity to solidify the material and prevent continued flow, for example, using water, pH or temperature to induce curing.

One example of a light-activated formulation is one that comprises an acrylate (e.g., hexyl acrylate, etc.), a diacrylate (e.g., PDMS diacrylate, poly(ethylene glycol) diacrylate, 1,4-butanediol diacrylate, etc.), and a photoinitiator (e.g., 2,4,6-trimethylbenzoyl diphenylphosphine oxide, etc.). The polymer molecular weight between crosslinks and mechanical properties can be controlled by controlling the molecular weight of the diacrylate and the relative concentrations of each component. Furthermore, cure may be achieved by copolymerizing acrylates with polymers or monomers containing moisture reactive functionality (functionality greater than 2), such as those having isocyanate or ethoxysilane functionality, among other possibilities.

Figure 2:
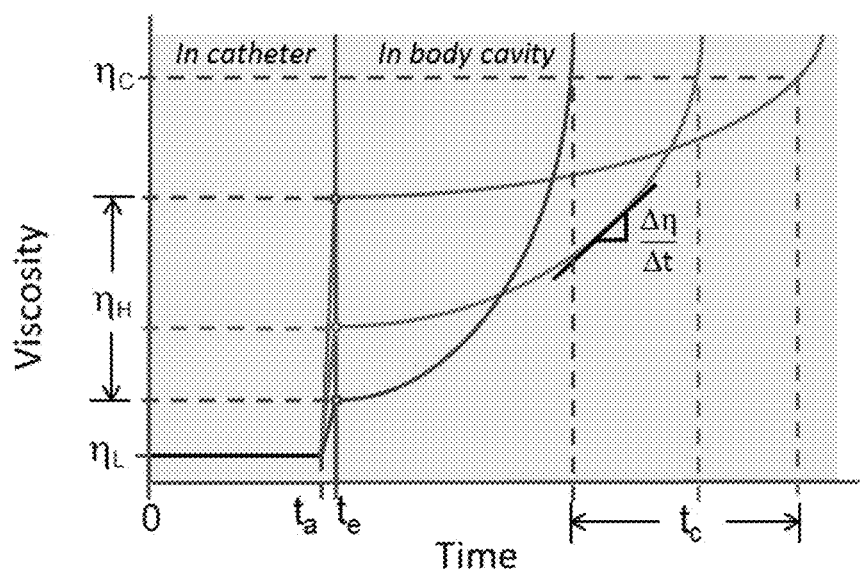
FIG. 2 is a schematic illustration like that of FIG. 1A, wherein viscosity as a function of time (and thus distance) is shown for three hypothetical formulations that reach different exit viscosities, in accordance with an embodiment of the present disclosure.

In various embodiments, the high viscosity reached at the catheter exit can be adjusted, depending on the application. For example, in cases where exit viscosity is on the lower side (e.g., to reduce the pressure required for delivery), it may be desirable to have a fast cure rate in order to enhance retention the formulation at the target site. In this regard, FIG. 2 shows viscosity as a function of time for three hypothetical formulations, each reaching differing exit viscosities. To provide adequate retention of the formulation at the target site, particularly for formulations that have lower exit viscosities ($\eta_H$), it may be desirable to select faster cure rates ($\Delta\eta/\Delta t$), which likewise results in shorter cure times ($t_C$).

Suitable catheters for the delivery of one or more low viscosity fluid(s) that react to high viscosities within the catheter are also described herein. Such catheters preferably deliver high viscosity material by application of a reasonable amount of pressure, preferably by the means of a hand powered device.

In various embodiments, delivery is enhanced by activating the formulation as close to the catheter tip as possible, for example, within 5 cm of the exit port of the catheter, within 2.5 cm of the exit port of the catheter, within 1 cm of the exit port of the catheter, or even within 0.5 cm or less of the exit port of the catheter, in some embodiment. For systems in which two low viscosity fluids are combined, the catheter is provided with means of mixing the fluids within a very short time and length scale.

Depending on the embodiment, the mixing mechanism employed in the catheter may be passive or active. Passive mixing relies only on the pressure from the fluid flow to create shear and increase the area of interfacial contact in conjunction with physical impediments (i.e., mixing elements), whereas in active mixing, additional energy is input into the system.

Passive mixing is advantageous in that the system is less complex. Examples of passive mixers that may be employed in catheter systems described herein include static helical mixers, lamination mixers, and T-mixers.

Figure 4A:
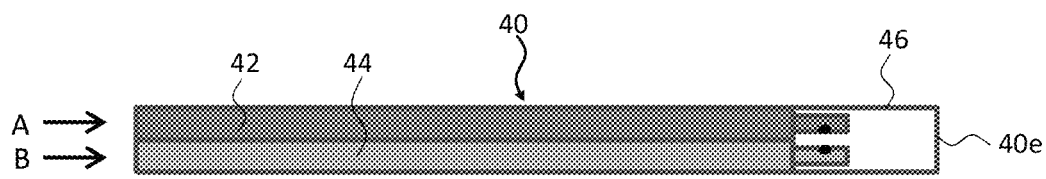
FIG. 4A is a schematic illustration of a dual lumen mixing catheter, in accordance with an embodiment of the present disclosure.
Figure 4B:
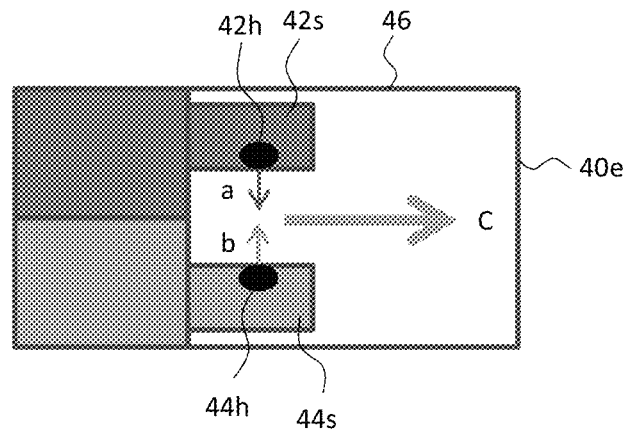
FIG. 4B is an enlarged view of a portion of FIG. 4A, illustrating mixing of first and second low viscosity fluids in order to form a high viscosity fluid.

An exemplary T-mixer catheter system, which has been shown in microfluidics research to provide mixing at low Reynolds numbers over a small length and time scale is schematically illustrated in FIGS. 4A and 4B, which shows dual lumen catheter 40, which has a first catheter lumen 42 carrying a first low viscosity fluid A and a second catheter lumen 44 carrying a second low viscosity fluid B. In this design, the two lumens 42, 44 in the dual lumen catheter 40 end in distal segments 42s, 44s that direct fluid a, b out of holes 42h, 44h in the distal segments 42s, 44s in a direction that is perpendicular to the final flow direction of the mixed material C for the exit port 40e of the catheter 40. The streams a, b emerging from the holes 42h, 44h are aligned and such that the streams collide with one another. The intersection of the two flows a, b causes rapid mixing in a mixing volume confined by the sheath 46. The holes 42h, 44h preferably have a width that is small enough to create sufficient fluid velocity to cause efficient mixing. In certain embodiments, the holes 42h, 44h may range, for example, from 0.05 mm-0.5 mm in diameter, preferably ranging from 0.05 mm-0.25 mm. Since each hole 42h, 44h is formed in a side wall of each distal segment 42s, 44s, the distance traveled by each fluid is the thickness of the side wall, minimizing the increase in system pressure associated with the distal segments 42s, 44s. The exit velocity of the two fluids a, b and the distance from the catheter exit port 40e may be adjusted based on the amount of mixing desired.

Active mixing, although somewhat more complex, is advantageous in terms of mixing efficiency and required input pressure over passive mixing. Since the energy to mix the two fluids is supplied externally, the pressure required for fluid flow is not increased. An example of an active mixer is a rotating hoop that creates shear at the walls of the catheter, enhancing mixing of the two fluids.

Figure 6:
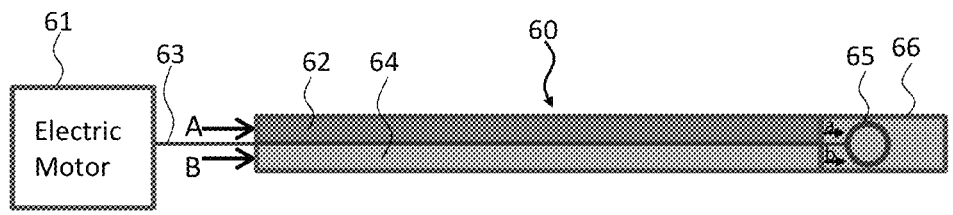
FIG. 6 is a schematic illustration of dual lumen catheter having dynamic mixing capability, in accordance with an embodiment of the present disclosure.

A system of this type is schematically illustrated in FIG. 6, which shows a dual lumen catheter 60, which has a first catheter lumen 62 carrying a first low viscosity fluid A and a second catheter lumen 64 carrying a second low viscosity fluid B. The streams of fluid a, b emerging from the lumens 62, 64 are mixed in a volume confined by sheath 66 using a rotating hoop 65. Rotation of the hoop 65 is driven by an electrical motor 61 via a driveshaft 63. The outside diameter of the hoop 65 preferably matches as closely as possible the inside diameter of the catheter sheath 66 to minimize stagnant flow locations that may develop against the wall. In some embodiments, the driveshaft is preferably made up of a braided torque wire that has close to 1:1 torque to eliminate potential binding.

Figure 5A:
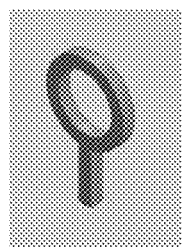
FIGS. 5A-5D are schematic illustrations of four dynamic mixing elements, in accordance with four embodiments of the present disclosure.
Figure 5B:
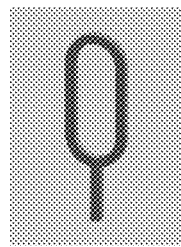
Figure 5C:
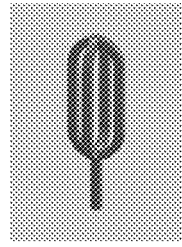
Figure 5D:
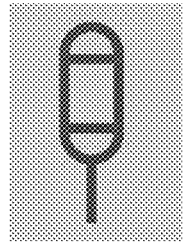

For viscous materials, open mixing element such as a hoop, or an open design analogous to those used for mixing cake batter, or low Reynolds number batch mixing (an anchor or helical ribbon) are much more efficient than traditional impellers. A single hoop allows for the removal and insertion of the mixing element in a dual lumen catheter because it is substantially planar. This is ideal for a system that requires guidewire access. Once the catheter is placed over the guidewire and the guidewire removed, the mixer may be inserted and placed through the same lumen if sized appropriately. In addition to a simple hoop design such as that shown in FIG. 5A, to improve the mixing length of the device (and minimize stagnant flows spots), the hoop may be elongated as shown in FIG. 5B. The hoop may also be rectangular in shape, if desired. If additional shear is desired to mix the components, additional structures can be added as shown in FIGS. 5D and 5E.

In alternative embodiments, the need for a driveshaft may be avoided by using a magnetically driven impeller. The impeller may contain a magnet and be driven by an electromagnetic coil placed adjacent the magnet near the tip of the catheter.

Figure 7:
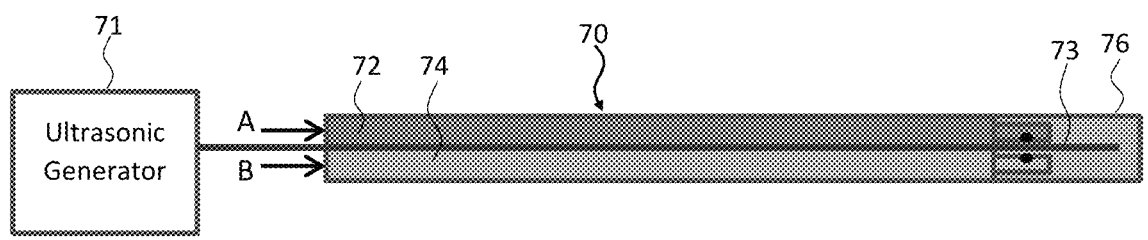
FIG. 7 is a schematic illustration of dual lumen catheter having ultrasonic mixing capability, in accordance with another embodiment of the present disclosure.

In further alternative embodiments, the two fluids may be mixed at the tip of the catheter using an acoustic stirring effect produced by ultrasonic waves. A system of this type is schematically illustrated in FIG. 7, which shows a dual lumen catheter 70, which has a first catheter lumen 72 carrying a first low viscosity fluid A and a second catheter lumen 74 carrying a second low viscosity fluid B. An ultrasonic frequency generator 71 is connected to a wire 73 that travels the length of the catheter 70 and extends into the mixing chamber defined by the sheath 76 where the two fluids come together. The ultrasonic waves emitted from the wire 73 cause the two components to become well mixed. In the particular embodiment shown, as in FIGS. 4A-4B discussed above, each of the two lumens 72, 74 in the dual lumen catheter 70 ends in a segment that forces the material out perpendicular to the final flow direction. The two streams collide with each other and the ultrasonic mixing wire 73 which emits an ultrasonic frequency causing the two components A, B to be acoustically mixed as well.

Delivery can be enhanced by increasing the diameter of the catheter tip to counteract the increase in pressure associated with the increasing viscosity. In some embodiments, >50% of the pressure drop in the system occurs at the active tip (e.g., within the last 1cm) where the material viscosity increases. For circular conduits, pressure drop is inversely proportional to the fourth power of the radius (i.e., $\alpha\ r^{-4}$). Therefore, a slight increase in width at the catheter tip can substantially reduce the overall pressure of the system.

In order to allow the delivery of the material in a minimally invasive way, the catheter may beneficially have a smooth and constant outer diameter (OD) upon insertion. To reduce system pressure, however, it is desirable in some embodiments that the catheter tip be configured to be enlarged post-insertion and at the target site. This can be achieved in various ways including the use of an elastic membrane or a self-expanding tip that is housed in a sheath, among other options. In certain embodiments, the mixing chamber of the catheter is located just upstream of the expandable tip to allow for adequate mixing and shearing at the catheter wall. Two of these concepts are schematically illustrate in FIGS. 8A-8B and 9A-9B.

Figure 8A:
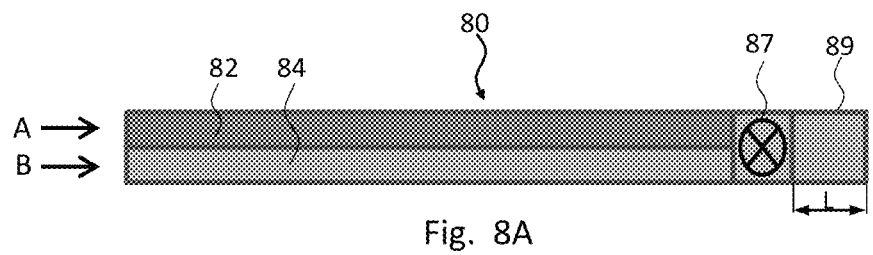
FIGS. 8A-8B are schematic illustrations of a dual lumen catheters having an elastic, expandable catheter tip, in accordance with an embodiment of the present disclosure.
Figure 8B:
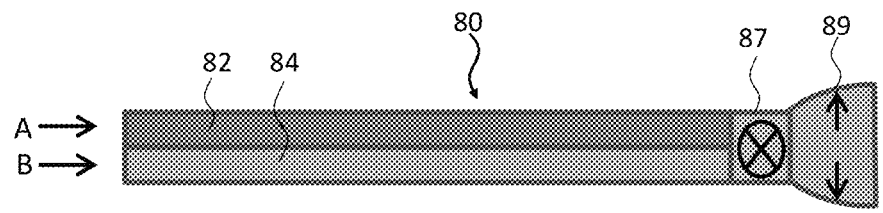

Turning to FIG. 8A, a system is schematically shown which includes a dual lumen catheter 80, which has a first catheter lumen 82 carrying a first low viscosity fluid A and a second catheter lumen 84 carrying a second low viscosity fluid B. The catheter includes a mixing chamber 87 and an elastic catheter tip 89 formed of an elastic material such as silicone (e.g., PDMS), Latex, EPDM (ethylene propylene diene monomer) rubber, and other rubbers, among other possibilities. The elastic catheter tip 89 is attached just distal to the mixing chamber 87 and has a resting (unstressed) outer diameter approximately the same as the remainder of the dual lumen catheter 80. As discussed above, when the first and second low viscosity fluids A, B mix they form a highly viscous material that will dramatically increase the system pressure. This increase in pressure will stretch the elastic material of the catheter tip 89 as shown in FIG. 8B. As the material of the catheter tip 89 stretches, the inner diameter of the catheter tip 89 increases, resulting in a reduction of pressure. The elasticity of the material forming the catheter tip 89 can be tailored to allow a specific and robust amount of stretch based on the pressure experienced. In certain embodiments, the elastic tip ranges from 0.1-5 cm in length L, and preferably ranges from 0.1-1 cm in length L.

Figure 9A:
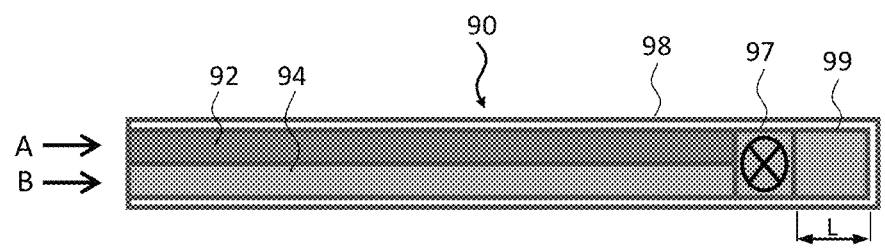
FIGS. 9A-9B are schematic illustrations of a dual lumen catheters having an expandable catheter tip that is opened by retraction of a sheath, in accordance with another embodiment of the present disclosure.
Figure 9B:
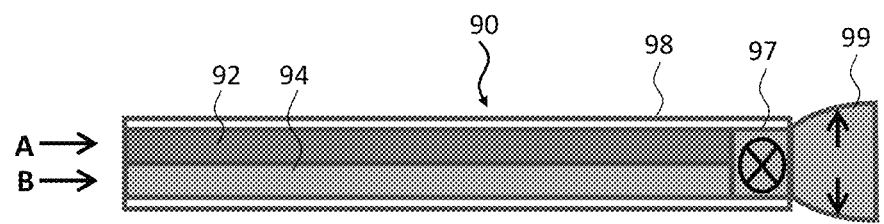

Another system in which the catheter tip is self-expanding is schematically illustrated in FIG. 9A, which shows a dual lumen catheter 90, which has a first catheter lumen 92 carrying a first low viscosity fluid A and a second catheter lumen 94 carrying a second low viscosity fluid B. The catheter includes a mixing chamber 97 and a self-expanding catheter tip 99. The self-expanding catheter tip 99 is flared and housed in a retractable sheath 98. The tip can 99 may be formed of a self-expanding material that self-expands (e.g., due to an elastic shape memory effect), or the tip 99 may comprise a structure similar to a covered self-expanding stent. When the sheath is retracted as shown in FIG. 9B, the tip 99 self-expands into a flared configuration. After the procedure is complete, the self-expanding tip 99 can then be pulled back into the sheath, compressing the tip 99 to a reduced diameter for removal. In certain embodiments, the elastic tip ranges from 0.1-5 cm in length L, and preferably ranges from 0.1-1 cm in length L. In an alternative embodiment, the tip may comprise a pre-formed thin plastic flare that is folded and opens fully when material is injected.

For heat-activated systems, in some embodiments, a delivery catheter may be provided which is configured to apply heat only at the tip of the catheter, preferably, within 5 cm of the exit port of the catheter. In one embodiment, a heat source comprises a heated wire that runs through the catheter. The wire is uninsulated within 5 cm of the exit port, but is insulated elsewhere, thus transferring heat to the formulation at the distal tip of the catheter. The wire can be formed into any shape or pattern necessary to provide suitable heat transfer. For example, the wire can be coiled around the tip, either internal or external or embedded within the wall of the lumen, or the wire may be provided within the catheter lumen, for example, in the form of mesh or grid that the formulation is passed through (thereby providing enhanced heat transfer).

In another embodiment of the delivery catheter, radiofrequency (RF) energy may be used as the heat source. For example, an RF source may be employed that transmits the desired frequency along a cable and emits the energy only within 5 cm of the exit port, heating the formulation and initiating reaction of the formulation.

For light-activated systems, the delivery catheter can be designed to provide UV or visible light within 5 cm of the exit port. In one embodiment, light can be provided using power supply connected to a light emitting diode (LED). In some embodiments, the LED is positioned to directly provide illumination within 5 cm of the exit port. In other embodiments, the LED is further connected to a thin fiber optic cable. The fiber optic cable runs down the center of the catheter and terminates preferably within 5 cm of the exit port. Light at a specified wavelength, supplied by the (LED), will either exit the LED directly or exit the fiber optic cable and initiate reaction of the formulation. The wavelength and intensity of the light, as well as the numerical aperture of the fiber optic cable, may all be selected to provide the ideal curing profile of the formulation In various embodiments described herein, heat may be applied along the length of the catheter to maintain a low formulation viscosity, but then rapidly cooled within the catheter tip to increase the exiting viscosity.

In various embodiments described herein, for a two part system, a first low viscosity fluid A and a second low viscosity fluid B are heated separately in the catheter, in order to lower the viscosity of fluids A and B for ease of delivery. Once fluid A is mixed with fluid B near the exit port, the mixture may be heated further, if desired, to speed up the reaction of the two parts and increase the exiting viscosity.

Although various embodiments are specifically illustrated and described herein, it will be appreciated that modifications and variations of the present disclosure are covered by the above teachings and are within the purview of the appended claims without departing from the spirit and intended scope of the invention.

The invention claimed is:

1. A system comprising (a) a catheter comprising a first lumen having a proximal end configured to receive a first low viscosity fluid, a distal end and an exit port proximal to a distal end of the catheter; and (b) a source of thermal energy, radiofrequency energy or light configured to expose the low viscosity fluid to heat, radiofrequency or light, respectively, and convert the low viscosity fluid to a high viscosity fluid, wherein the system is configured to form the high viscosity fluid only at the distal end of the catheter within 5 cm of the exit port.

2. The system of claim 1, wherein the high viscosity fluid is configured to cure into a solid material after delivery from the exit port of the catheter.

3. The system of claim 1, wherein the first low viscosity fluid comprises a polyisocyanate and an amine catalyst and wherein the first low viscosity fluid is converted to the high viscosity fluid by exposure to heat.

4. A system comprising (a) a catheter comprising a first lumen having a proximal end configured to receive a first low viscosity fluid, a distal end and an exit port proximal to a distal end of the catheter; and (b) a source of light configured to expose the low viscosity fluid to light and convert the low viscosity fluid to a high viscosity fluid within 5 cm of the exit port, wherein the first low viscosity fluid comprises an acrylate and a diacrylate and wherein the first low viscosity fluid is converted to the high viscosity fluid by exposure to UV light.

5. A system comprising (a) a catheter comprising a first lumen having a proximal end configured to receive a first low viscosity fluid, a distal end and an exit port proximal to a distal end of the catheter; and (b) a source of light configured to expose the low viscosity fluid to light, and convert the low viscosity fluid to a high viscosity fluid within 5 cm of the exit port, wherein the first low viscosity fluid is a light activated formulation comprising an acrylate, a diacrylate and a photo initiator.

6. The system of claim 5, wherein the first low viscosity fluid is an acrylate selected from poly(dimethyl)siloxane diacrylate, poly(ethylene glycol) diacrylate and 1,4-butanediol acrylate; and the photo initiator is 2,4,6-trimethylbenzoyl biphenylphosphine oxide.

7. The system of claim 5, wherein the first low viscosity fluid is converted to a high viscosity fluid by irradiating the first low viscosity fluid with UV or visible light.

8. A system comprising (a) a catheter comprising a first lumen having a proximal end configured to receive a first low viscosity fluid, a distal end and an exit port proximal to a distal end of the catheter; and (b) a source of thermal energy, radiofrequency energy or light configured to expose the low viscosity fluid to heat, radiofrequency or light, respectively, and convert the low viscosity fluid to a high viscosity fluid within 5 cm of the exit port, wherein the first low viscosity fluid comprises a heat activated formulation comprising a multi-functional isocyanate mixed with an amine catalyst and wherein the multi-functional isocyanate is a silicone triisocyanate and the amine catalyst is 1,8-diazabicycloundec-7-ene.

9. A system comprising (a) a catheter having a proximal and a distal end and comprising first and second lumens, at least one of the first and second lumens terminating in an exit port proximal to the distal end of the catheter; (b) a mixing element located in the catheter at a portion of the distal end of the catheter proximal to the exit port and fluidly communicating with the first and second lumens; (c) a power source configured to deliver mixing energy to the mixing element; and (d) first and second low viscosity fluids, wherein the catheter is configured to receive the first low viscosity fluid at the proximal end of the first lumen and receive the second low viscosity fluid at the proximal end of the second lumen and to mix the first and second low viscosity fluids between the exit port and the portion of the catheter where the mixer and first and second lumens are in fluid communication; wherein the first and second low viscosity fluids are configured to form a high viscosity fluid when mixed.

10. The system of claim 9, wherein the first and second low viscosity fluids are configured to form a high viscosity fluid having a viscosity from 100,000 to 1,000,000 cP as measured using a parallel plate rheometer with a shear rate of between a 1 and 10 $s^{-1}$ when mixed.

11. The system of claim 9, wherein the mixing energy is mechanical energy, acoustic energy, electromechanical energy or radiofrequency.

12. The system of claim 9, wherein the mixing element is a rotating hoop.

13. The system of claim 9, wherein the mixing element is a magnetically driven impeller.

14. The system of claim 9, wherein the power source is an ultrasonic wave generator.

15. The system of claim 8, wherein the catheter is configured to mix the first low viscosity fluid and the second low viscosity fluid within 5 cm of the exit port.

16. The system of claim 8, wherein one of the first and second low viscosity fluids comprises a curing agent that causes crosslinking within the high viscosity fluid after delivery from the exit port.

17. The system of claim 16, wherein the curing agent is activated upon exposure to water.

* * * * *